(12) United States Patent
Lee et al.

(10) Patent No.: US 7,764,482 B2
(45) Date of Patent: Jul. 27, 2010

(54) VITAMIN ION GENERATOR

(75) Inventors: Sung Hwa Lee, Changwon-shi (KR); Seong Hwan Lee, Changwon-shi (KR); Ok Chun Hyun, Sasang-ku Busan (KR)

(73) Assignee: LG Electronics Inc., Seoul (KR)

( * ) Notice: Subject to any disclaimer, the term of this patent is extended or adjusted under 35 U.S.C. 154(b) by 1264 days.

(21) Appl. No.: 11/297,365

(22) Filed: Dec. 9, 2005

(65) Prior Publication Data
US 2006/0137976 A1  Jun. 29, 2006

(30) Foreign Application Priority Data
Dec. 13, 2004  (KR)  ............... 10-2004-0105058

(51) Int. Cl.
*H01T 23/00* (2006.01)
(52) U.S. Cl. .......................... 361/230; 96/95
(58) Field of Classification Search ......... 361/226–228, 361/230, 231; 239/706, 690, 3; 315/111.81, 315/111.01; 96/222, 223, 155, 52, 53, 95; 250/423 R
See application file for complete search history.

(56) References Cited

U.S. PATENT DOCUMENTS

| | | | |
|---|---|---|---|
| 7,120,006 B2 * | 10/2006 | Sekoguchi et al. | 361/230 |
| 7,312,973 B2 * | 12/2007 | Sekoguchi et al. | 361/231 |
| 7,368,003 B2 * | 5/2008 | Crapser et al. | 96/222 |
| 7,408,562 B2 * | 8/2008 | Kotsuji | 361/231 |
| 2006/0131449 A1 * | 6/2006 | Azukizawa et al. | 239/690.1 |
| 2006/0214020 A1 * | 9/2006 | Suda et al. | 239/3 |

* cited by examiner

*Primary Examiner*—Douglas W Owens
*Assistant Examiner*—Ephrem Alemu
(74) *Attorney, Agent, or Firm*—Birch, Stewart, Kolasch & Birch LLP (57) ABSTRACT

An ion generator is provided which includes a discharge electrode, a ground electrode and vitamins housed in the discharge electrode which is adapted to be installed inside a discharge outlet of an air conditioner. A power supply for applying power is connected to the discharge electrode. A reservoir for storing water generated in the heat exchanger of the air conditioner supplies water to the discharge electrode. The water housed in the reservoir is transferred to the discharge electrode. The vitamins housed in the discharge electrode are dissolved in the water, exposed to the surface of the discharge electrode and discharged in the direction of the ground electrode by power applied to the discharge electrode. The discharged vitamin ions are externally discharged from the air conditioner by a ventilator of the air conditioner. The vitamin C ions are coupled with the electrons from the discharge electrode. The vitamin ion generator prevents the electrons discharged from the discharge electrode from generating a large quantity of $OH^-$ by neutralizing $OH^-$ generated by electron collision to prevent free radical operations in a human body, and transmits the vitamin C ions to the human body for anti-oxidization.

7 Claims, 8 Drawing Sheets

L-ascorbic acid          L-dehydroascorbic acid

VITAMIN ION GENERATOR

TECHNICAL FIELD

The present invention relates to an anion generator, and more particularly, to a vitamin ion generator which can generate ionized vitamins as well as anions.

BACKGROUND ART

In general, an anion generator makes a current flow through a discharge electrode and a ground electrode, so that electrons can be transferred from the discharge electrode to the ground electrode. The transferred electrons ionize contact substances to have a negative polarity.

Here, anions generated when the electrons discharged from the discharge electrode and transferred to the direction of the ground electrode are coupled with the air or other substances, neutralize static electricity having a positive polarity, activate cells of a human body, purify blood, and palliate pain. Therefore, the anions absorb attention.

Among the anions, $OH^-$ couples with bacteria to destroy cell walls of bacteria, thereby obtaining sterilization and disinfection effects. $OH^-$ has a higher oxidization performance than $O_3$ and $Cl_2$ by two times, and sterilizes bacteria with a higher oxidization speed than $O_3$ and ultraviolet rays by 200 times and 180 times, respectively. Thus $OH^-$ generated by the anion generator has attained growing attention.

When the electrons discharged from the discharge electrode collide with $H_2O$ of the air with a certain energy, the $H_2O$ is divided into $H^+$ and $OH^-$. $H^+$ is coupled with the electrons from the discharge electrode to form $H_2$, and volatilized. $OH^-$ sterilizes the bacteria of the air by oxidizing the cell walls of the bacteria.

However, although $OH^-$ is an oxygen compound having free electrons and sterilizes bacteria, it is also known as a free radical, permeating into the human body and generating oxidization reactions, for example, destroying cell walls.

Exemplary free radicals include $O_2^-$, $OH^-$, $H_2O_2^+$ and $LOOH^-$. $OH^-$ has the highest oxidization performance.

Figure 1:
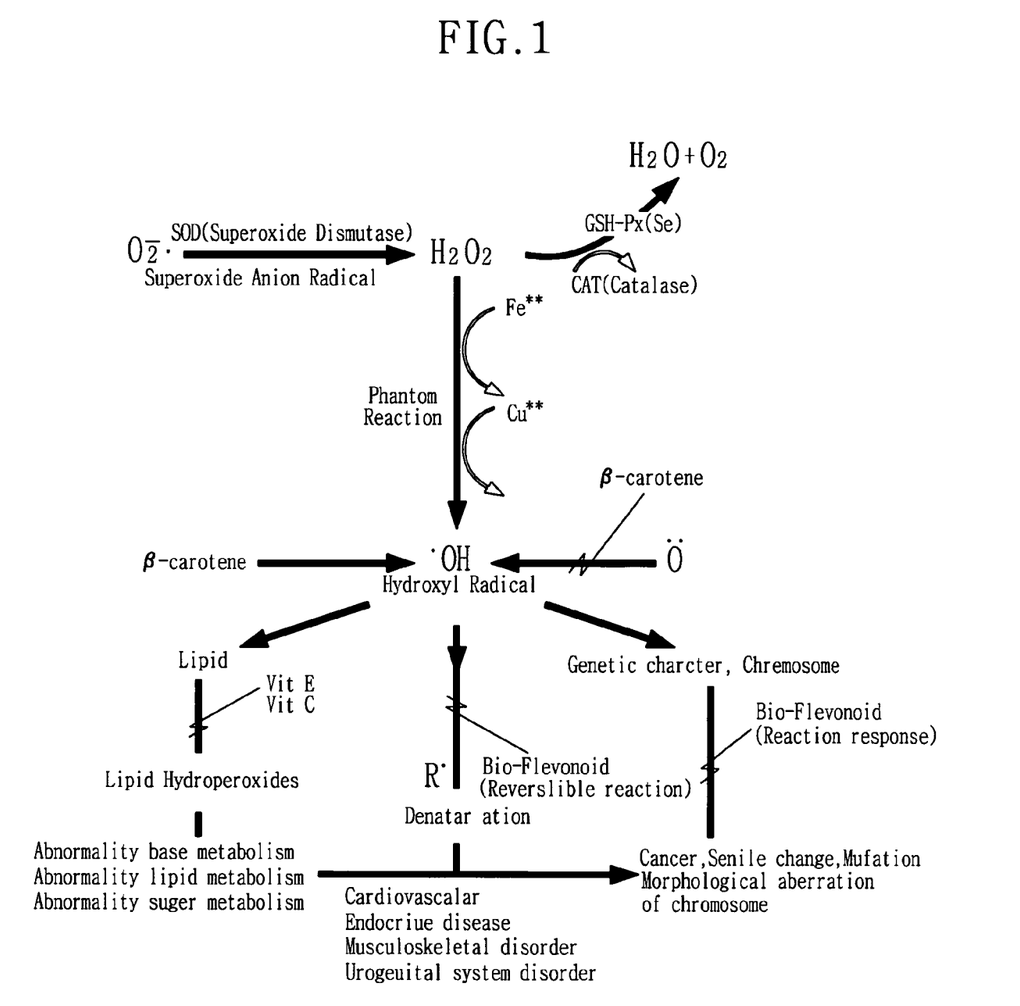
FIG. 1 is an operational state view illustrating influences of OH— on a human body.

As illustrated in FIG. 1, $OH^-$ that is the free radical, has detrimental effects on the human body, for example, it damages DNA, destroys the cell walls of lipid, chain-reacts with products and deforms protein. $OH^-$ also influences the generation of cancer, aging and the generation of mutant.

Accordingly, the electrons discharged from the discharge electrode of the anion generator react with $H_2O$ of the air, and the $H_2O$ decomposes into $H_2$ and $OH^-$. Some of $OH^-$ sterilizes the bacteria of the air, and the other penetrate into the human body and exerts a bad influence on the skin of the human body, as the free radical.

The anion generator installed in each house to generate the anions and remove and sterilize alien substances must generate $OH^-$ for sterilization by decomposing $H_2O$ of the air. As a result, there are strong demands for preventing damages caused by excessive $OH^-$ penetrating into the human body.

DISCLOSURE OF THE INVENTION

The present invention is achieved by solving the above problems. An object of the present invention is to provide a vitamin ion generator which can restrict and neutralize $OH^-$ generated by discharged electrons, while discharging vitamins which operate as antioxidants in a human body.

Another object of the present invention is to provide a vitamin ion generator which can neutralize $OH^-$ generated by discharged electrons in the air, while discharging vitamin C having an antioxidant property.

Yet another object of the present invention is to provide a vitamin ion generator which can discharge vitamin C operating as an antioxidant to penetrate into a human body and neutralize $OH^-$ generated by discharged electrons.

Yet another object of the present invention is to provide a vitamin ion generator which is installed in an air conditioner.

In order to achieve the above-described objects, the present invention includes the steps of: dissolving vitamins in water; exposing the dissolved vitamins on a surface of a discharge electrode, and discharging vitamins from the discharge electrode by applying power to the discharge electrode and a ground electrode; and reacting the vitamins from the discharge electrode with electrons on the discharge electrode.

According to another aspect of the present invention, the vitamins are vitamin C which is soluble in water and neutralizes free radicals such as $OH^-$.

According to yet another aspect of the present invention, the discharge electrode of the ion generator is made of a ceramic having a plurality of pores.

According to yet another aspect of the present invention, a housing groove is formed by hollowing out the inner portion of the discharge electrode, and the vitamins are housed in the housing groove.

According to yet another aspect of the present invention, the vitamins housed in the housing groove are dissolved by water supplied to the housing groove and are exposed to the outer space of the discharge electrode through a plurality of pores formed on the discharge electrode, by a capillary phenomenon.

According to yet another aspect of the present invention, a vitamin C derivative generated by adding Na to vitamin C is used to improve stability and the coupling performance of vitamin C.

According to yet another aspect of the present invention, the ion generator is installed in an air conditioner for discharging the vitamin ions, when the air cooled or heated in the air conditioner is discharged by the operation of the air conditioner.

BRIEF DESCRIPTION OF THE DRAWINGS

The present invention will become better understood with reference to the accompanying drawings which are given only by way of illustration and thus are not limitative of the present invention, wherein.

BEST MODE FOR CARRYING OUT THE INVENTION

A vitamin ion generator in accordance with the present invention will now be described in detail with reference to the accompanying drawings.

Figure 2:
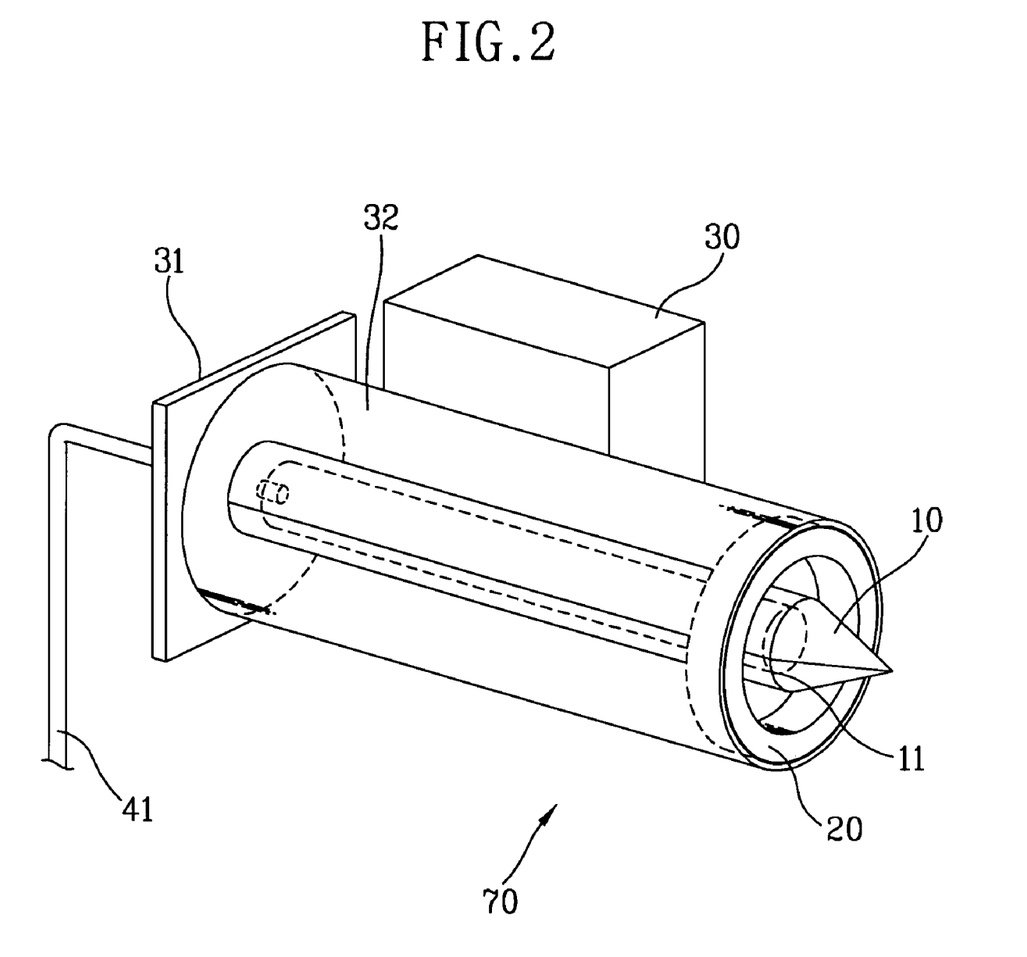
FIG. 2 is a perspective view illustrating a vitamin ion generator in accordance with the present invention.
Figure 3:
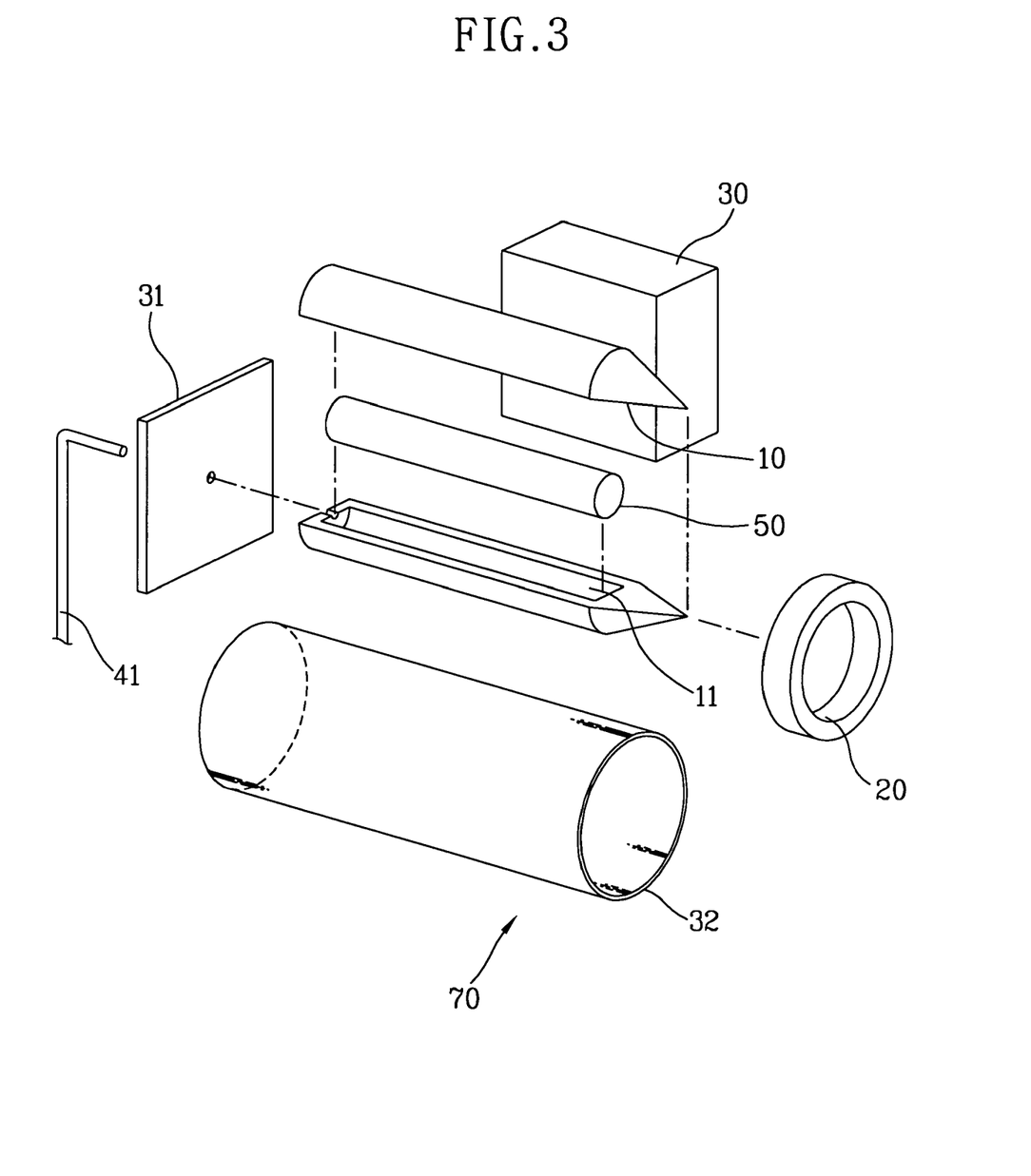
FIG. 3 is a disassembly perspective view illustrating the vitamin ion generator in accordance with the present invention.
Figure 4:
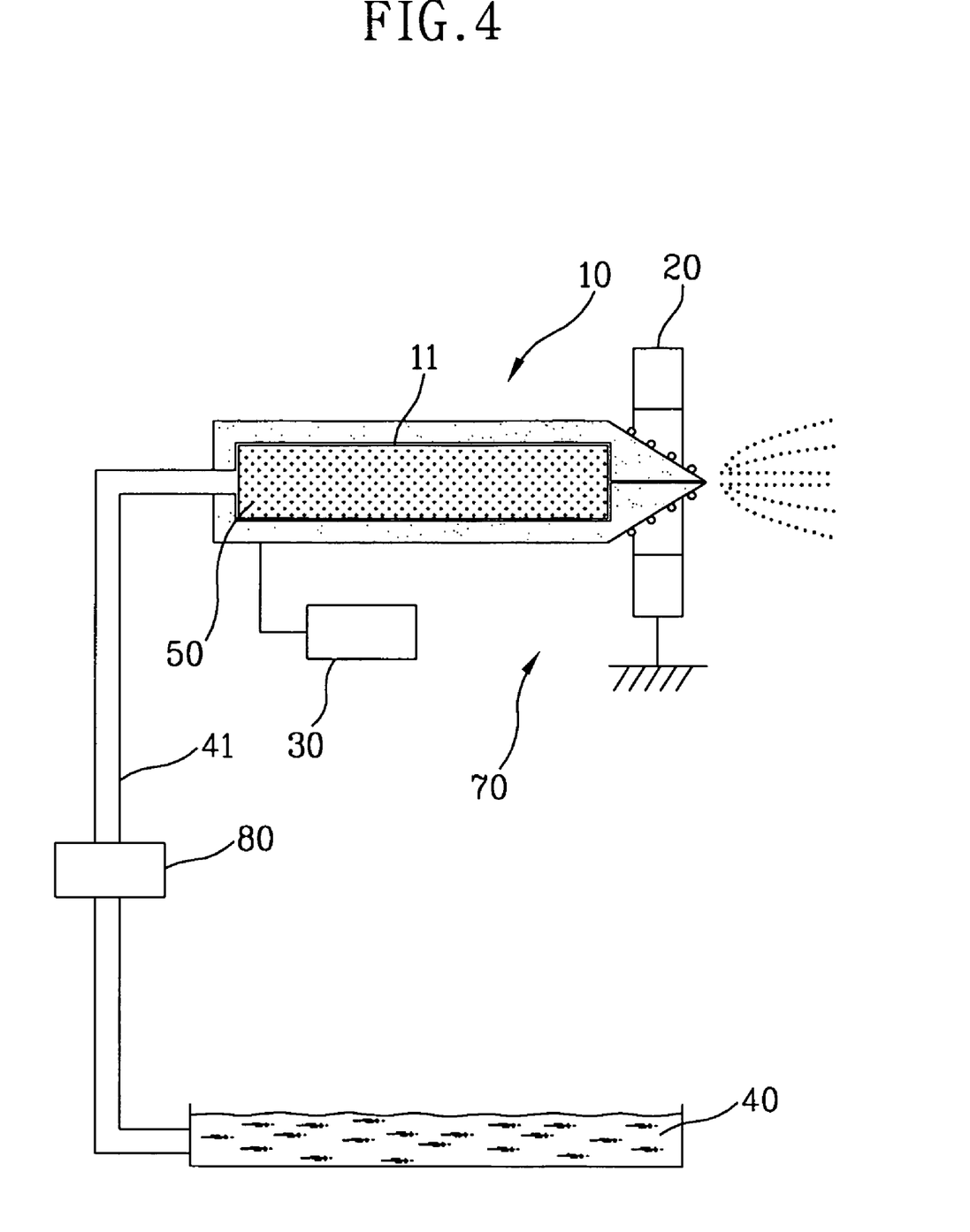
FIG. 4 is a cross-sectional view illustrating the vitamin ion generator in accordance with the present invention.
Figure 5:
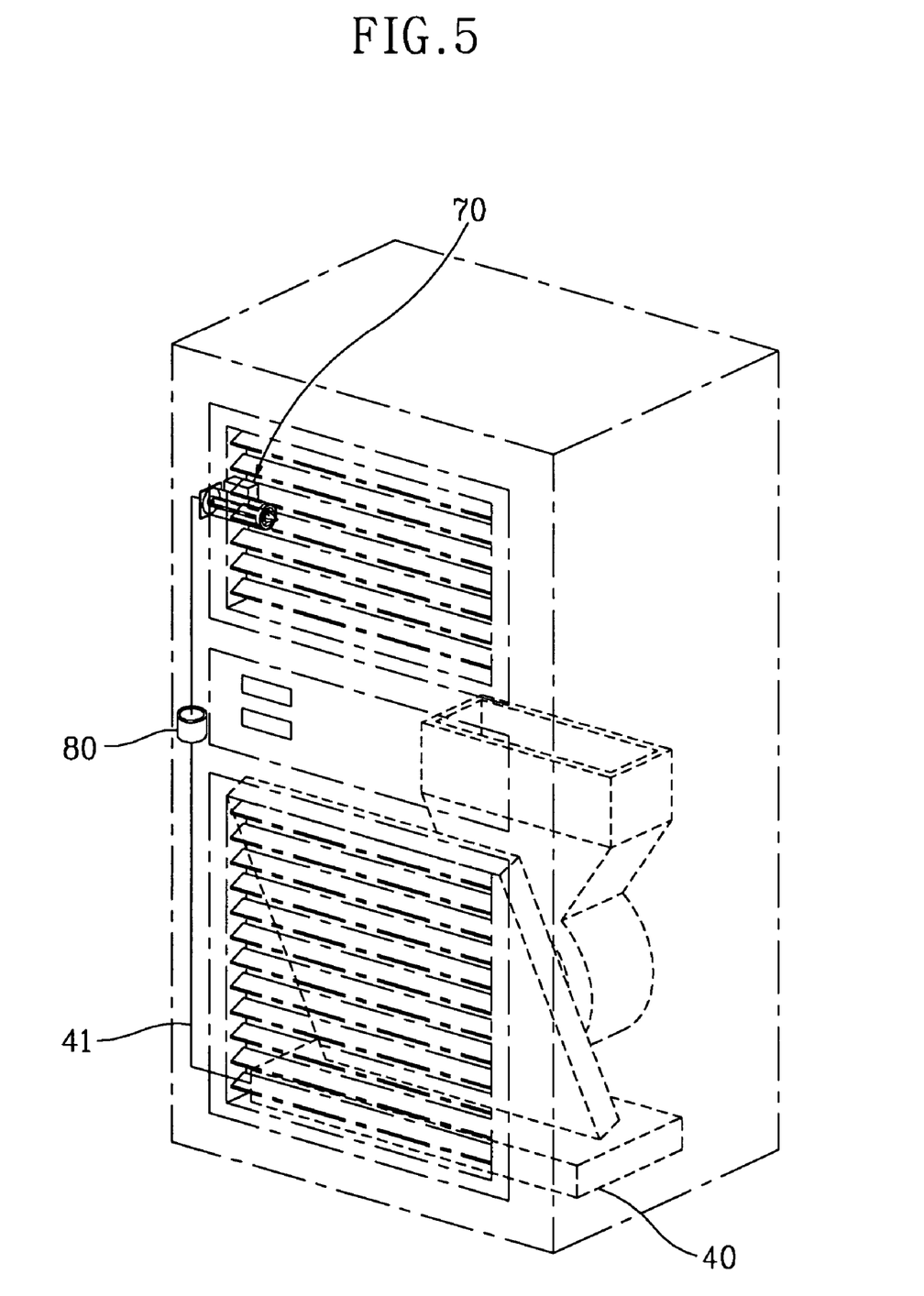
FIG. 5 is a perspective view illustrating an air conditioner on which the vitamin ion generator has been mounted in accordance with the present invention.
Figure 6:
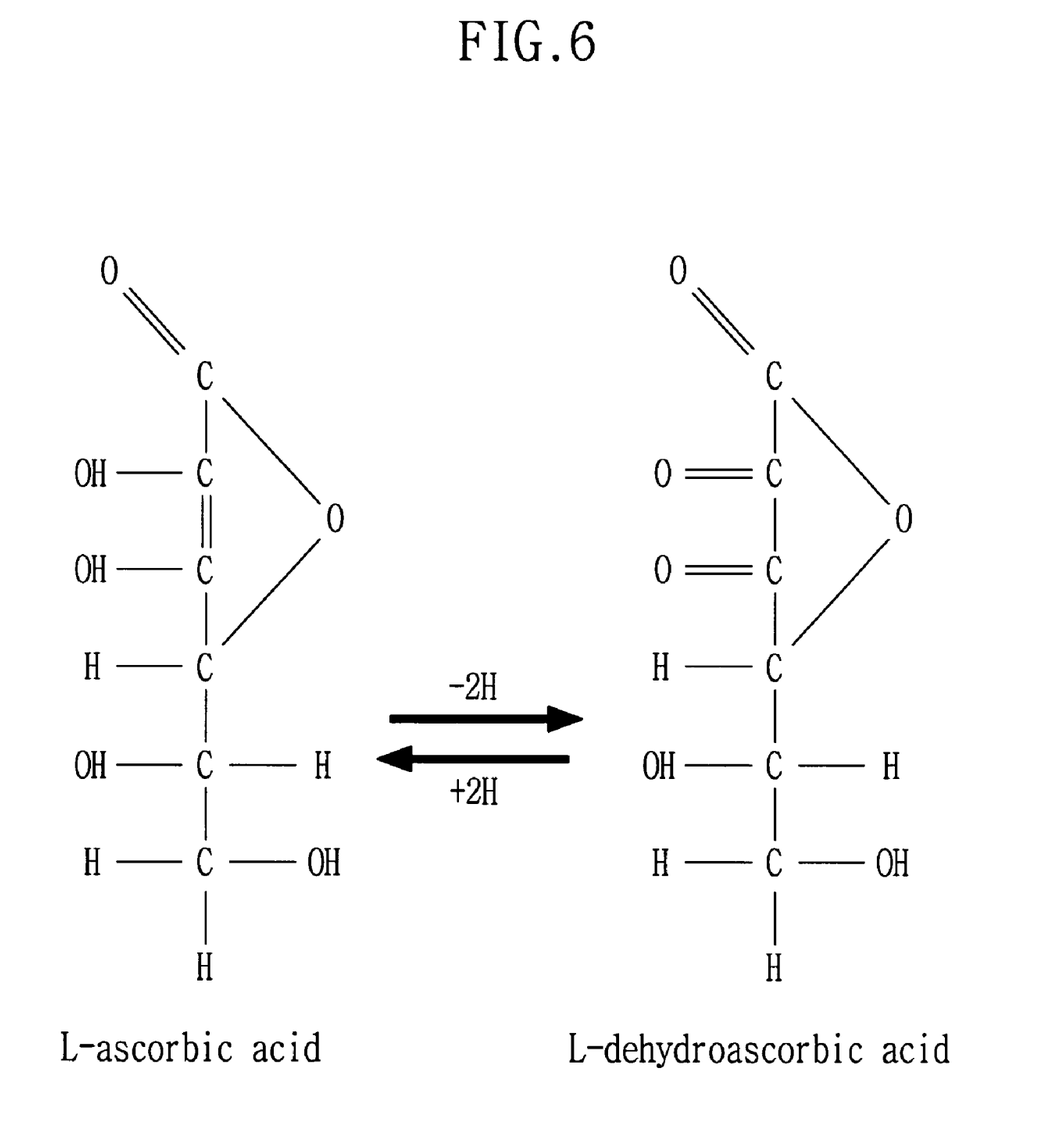
FIG. 6 is a view showing molecular formulae of vitamin C in accordance with the present invention.
Figure 7:
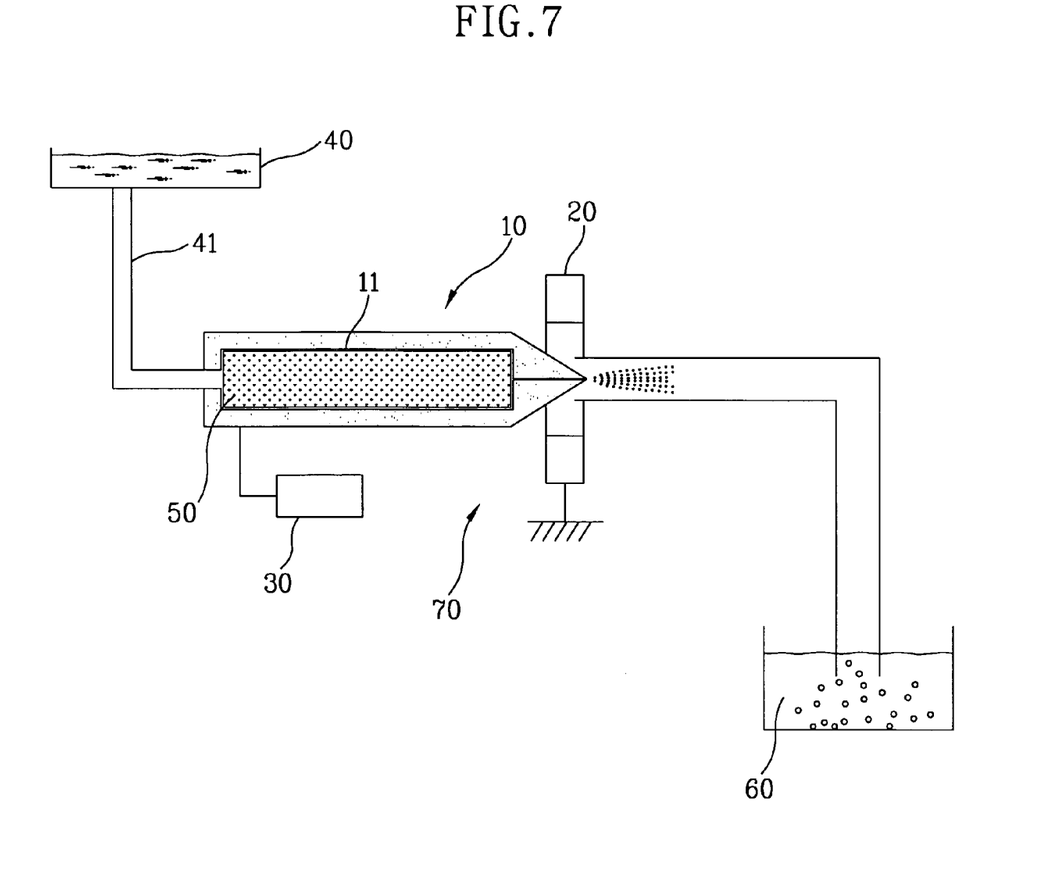
FIG. 7 is a structure view illustrating a vitamin ion measuring apparatus in accordance with the present invention.
Figure 8:
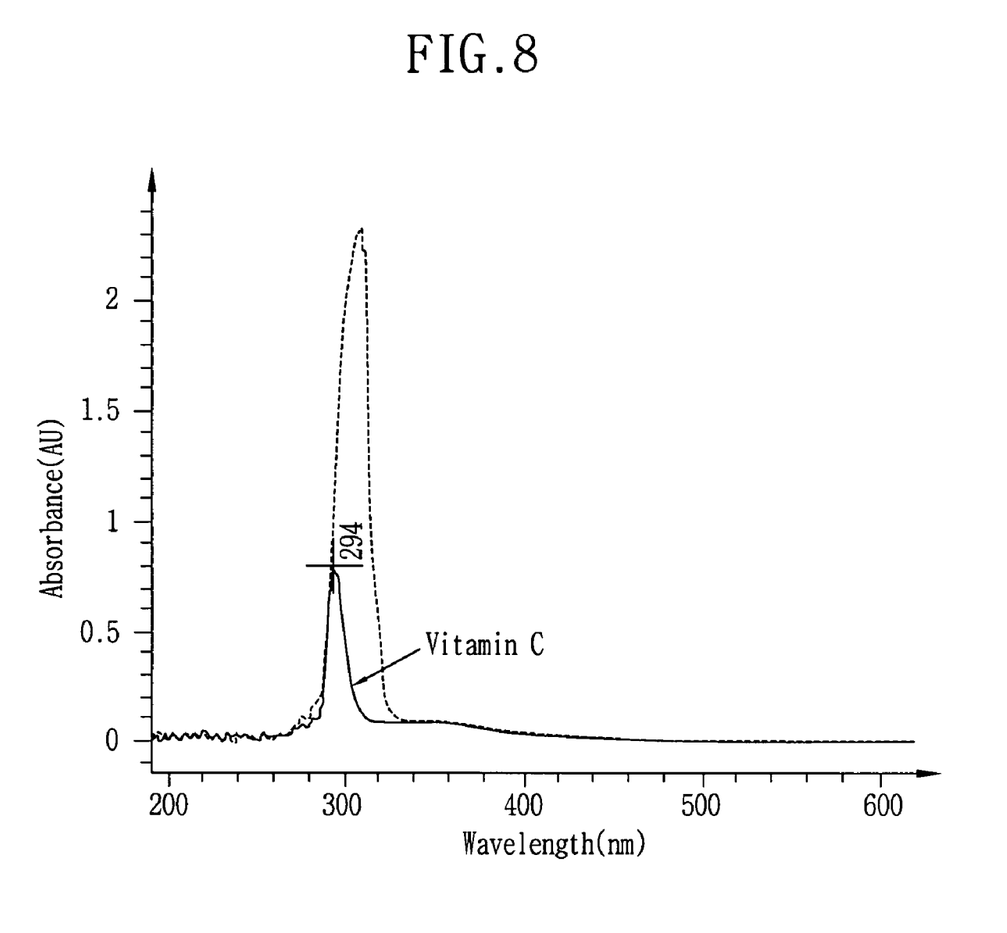
FIG. 8 is a graph showing a mass spectrum of vitamin ions in accordance with the present invention.

FIGS. 2 to 4 illustrate the vitamin ion generator in accordance with the present invention, FIG. 5 illustrates an air conditioner on which the vitamin ion generator has been mounted in accordance with the present invention, FIG. 6 illustrates molecular formulae of vitamin C and a vitamin C intermediate in accordance with the present invention, FIG. 7 illustrates a vitamin ion measuring apparatus in accordance with the present invention, and FIG. 8 illustrates a mass of vitamin ions analyzed by a mass spectrometer in accordance with the present invention.

In accordance with the present invention, vitamins 50 are discharged from an anion generator 70.

The method for discharging the vitamins 50 from the anion generator 70 dissolves the vitamins 50 in water, and discharges the dissolved vitamins 50 from a discharge electrode 10 of the anion generator 70.

In more detail, the method for generating the anions containing the vitamins includes the steps of dissolving the vitamins in water, supplying the vitamin solution to the surface of the discharge electrode, discharging the vitamins, and coupling the vitamins with free electrons.

The step for dissolving the vitamins in water ionizes the water soluble vitamins 50 by dissolving the vitamins 50 in a solution such as water.

The step for supplying the vitamin solution to the surface of the discharge electrode exposes the vitamins 50 dissolved in water to the end or surface of the discharge electrode 10 performing the discharge operation.

The step for discharging the vitamins transfers the vitamins 50 exposed on the surface of the discharge electrode 10 to a direction of a ground electrode 20, by applying power 30 to the discharge electrode 10 and the ground electrode 20.

The step for coupling the vitamins with the free electrons couples the vitamins 50 transferred from the discharge electrode 10 to the ground electrode 20 with the free electrons discharged from the discharge electrode 10.

As illustrated in FIGS. 2 to 5, the vitamin ion generator 70 includes the discharge electrode 10, the ground electrode 20, the power supply 30, a reservoir 40 and the vitamins 50.

Here, the ion generator 70 is a general ion generator installed in an air conditioner. The ion generator 70 is individually formed to be easily mounted on the air conditioner, and housed in a casing not to interfere with other components of the air conditioner.

The discharge electrode 10 discharges the electrons to the direction of the ground electrode 20 by application of power 30. The discharge electrode 10 is formed in a cylindrical shape with a circular conical pointed end, and made of a ceramic material with a plurality of pores.

Preferably, the discharge electrode 10 is made of Fe, $Al_2O_3$, $SiO_2$, W, $TiB_2$, Ni, Cr, Co, or compounds thereof. Also, the discharge electrode 10 is made of a carbon compound containing the compound and C having self pores.

The plurality of pores are formed on the whole surface of the discharge electrode 10. The pores are minute tubes for inducing the capillary phenomenon.

Still referring to FIGS. 2 to 4, a housing groove 11 is formed in the discharge electrode 10.

Preferably, the discharge electrode 10 has its center cut to be divided into the upper and lower portions. Accordingly, the vitamins 50 can be inserted or discharged to/from the discharge electrode 10.

The housing groove 11 is formed by hollowing the whole inner portion of the discharge electrode 10, for housing the vitamins 50. The housing groove 11 is linked to a hose 41 discussed later.

The ground electrode 20 has a different polarity from the discharge electrode 10 in order to induce the flow of electrons from the discharge electrode 10. In this embodiment, the ground electrode 20 is formed in a ring shape around the pointed end of the discharge electrode 10, for inducing electron discharge of the discharge electrode 10. The ground electrode 20 is installed and grounded at a predetermined interval from the pointed end of the discharge electrode 10 in the rear portion of the pointed end of the discharge electrode 10, namely, in the center direction from the pointed end.

The power supply 30 is a general external power supply for applying power to the discharge electrode 10. In this embodiment, the power supply 30 includes a transformer connected to a special external power supply or a power supply of the air conditioner for boosting or dropping the voltage for the ion generator 70, thereby applying power to the ion generator 70 having a different power supply structure from the air conditioner.

The power supply 30 further includes a plate-shaped electrode 31 adhered to the rear surface of the discharge electrode 10, for applying power to the rear surface of the discharge electrode 10. Therefore, the power supply 30 applies power through a casing 32 explained later.

The reservoir 40 stores a solution such as water to supply the solution to the housing groove 11 of the discharge electrode 10. In this embodiment, since the ion generator 70 is installed in the air conditioner, the reservoir 40 is a condensed water collector installed at a lower portion of a heat exchanger, for collecting condensed water from the heat exchanger or a condenser.

The hose 41 is connected from one end of the reservoir 40 to the housing groove 11 of the discharge electrode 10.

The hose 41 is formed in a tube shape to be linked from one end of the reservoir 40 to the housing groove 11 formed by hollowing out the inner portion of the discharge electrode 10.

Preferably, a ventilator for ventilating the space between the discharge electrode 10 and the ground electrode 20 is further installed. Because the ion generator 70 is installed in the air conditioner, the ventilator is installed at one side portion of the ion generator 70, so that the air sent by the ventilator can send the vitamin ions from the discharge electrode 10 to the outer space of the air conditioner.

The casing 32 surrounds the discharge electrode 10 to prevent discharge or mis-operation of the discharge electrode 10 by external alien substances. In this embodiment, since the discharge electrode 10 is formed in a cylindrical shape, the casing 32 is formed in a cylindrical shape to surround the discharge electrode 10 at a predetermined interval from the outer circumference of the discharge electrode 10.

Preferably, one end of the casing 32 has an inner circumference identical to the outer circumference of the ground electrode 20 to house the ground electrode 20 corresponding to the discharge electrode 10.

In the case that the ion generator 70 is installed in the air conditioner or the like, the casing 32 is used as an adhesion medium means for adhering the ion generator 70 to the inner wall of the air conditioner.

FIG. 5 is a perspective view illustrating the air conditioner on which the ion generator 70 has been mounted in accordance with the present invention. The air conditioner is a general air conditioner for home use. The ion generator 70 is mounted in an indoor unit installed indoors.

Also, the ion generator 70 can be installed in a wall hanging type indoor unit or a ceiling type indoor unit as well as an air conditioner for industrial use.

The casing 32 of the ion generator 70 or the power supply 30 connected to one side of the casing 32 is adhered to one side inner wall of the air conditioner inside the discharge hole of the air conditioner by using brackets.

When the ion generator 70 is adhered to one side inner wall of the air conditioner, preferably, the pointed end of the discharge electrode 10 of the ion generator 70 faces the discharge hole center direction of the air conditioner.

In a state where the ion generator 70 is installed in the air conditioner, the hose 41 for supplying water into the discharge electrode 10 of the ion generator 70 is connected to the rear surface of the discharge electrode 10 to be linked to the housing groove 11 of the discharge electrode 10. The hose 41 linked to the rear surface of the discharge electrode 10 is connected to the reservoir 40 formed at the lower portion of the air conditioner.

The reservoir 40 is formed in a box shape having its top surface opened, for collecting condensed water from the heat exchanger of the air conditioner. The reservoir 40 is linked to one end of the hose 41, for supplying water.

Since the reservoir 40 of the air conditioner is installed at the lower portion of the ion generator 70 installed in the air conditioner, a pump 80 for pressurizing water of the reservoir 40 to reach the ion generator 70 is installed at the center of the hose 41.

The vitamin ion generator in accordance with the present invention will now be described in more detail.

In this embodiment, the vitamins 50 are water soluble vitamins. Preferably, the vitamins 50 are vitamin C which has an antioxidant property and is easily coupled with OH$^-$, as mentioned in the object of the invention, among the water soluble vitamins including vitamin B, vitamin B complex and vitamin C.

When the vitamin C ($C_6H_8O_6$) is dissolved in water ($H_2O$), H$^+$ of the vitamin C 50 is dissociated to generate dihydroascorbic acid that is an oxidization intermediate of the vitamin C 50. The oxidization intermediate of the vitamin C 50 is not stabilized due to high reactivity. Therefore, the vitamin C 50 is transformed into another compound, namely, a vitamin C 50 derivative.

TABLE 1

| Derivative | pH | Stability | Unit cost |
| --- | --- | --- | --- |
| Acid | 3.51 | ○ | ○ |
| Na | 8.02 | ○ | ◎ |
| Mg | 9.07 | ○ | △ |
| Glucoside | 3.02 | ○ | △ |
| $C_2H_5O$ | 3.95 | ○ | △ |

As shown in Table 1, the vitamin C 50 derivative ($C_6H_7NaO_6$) prepared by mixing Na which has high water solubility and a relatively low unit cost with the vitamin C 50 is used to stabilize the vitamin C 50.

Na serves as a binder for biding vitamin C 50 molecules as well as a stabilizing agent for preventing a chain reaction that the vitamin C 50 is dissolved in water and ionized by discharging H$^+$ that is an hydroxyl group and the ionized vitamin C 50 discharges H$^+$ again.

Preferably, the vitamin C 50 derivative is used in a powder type or a solid type by compressing the powder. Also, the vitamin C 50 derivative is formed in a cylindrical shape to be housed in the housing groove 11 of the discharge electrode 10 of the ion generator 70.

In a state where the vitamin C 50 derivative formed in a cylindrical shape is inserted into the housing groove 11 of the discharge electrode 10, the upper and lower portions of the discharge electrode 10 are coupled to each other.

As shown in FIG. 3, the power supply 30 is connected to one end of the discharge electrode 10. Another end of the discharge electrode 10 is linked to the hose 41 connected to the reservoir 40. The ground electrode 20 is installed at a predetermined interval from the discharge electrode 10 to induce electron discharge of the discharge electrode 10.

Water such as condensed water is stored in the reservoir 40 by the operation of the air conditioner. The water stored in the reservoir 40 flows through the hose 41 connected to one end of the reservoir 40, and flows into the discharge electrode 10 of the ion generator 70 by pressurization of the pump 80 connected to the hose 41. Here, the water flows into the discharge electrode 10 through the end of the discharge electrode 10.

The water flowing into the discharge electrode 10 dissolves the vitamin C 50 derivative ($C_6H_7NaO_6$) housed in the housing groove 11 of the discharge electrode 10.

The vitamin C 50 derivative ($C_6H_7NaO_6$) is dissolved in water and stabilized as neutral mono alkali salt ($C_6H_7NaO_6$) by discharging H$^+$.

The vitamin C 50 derivative dissolved in water is filled in the housing groove 11. The vitamin C 50 derivative ($C_6H_7NaO_6$) solution filled in the housing groove 11 contacts the plurality of minute pores of the discharge electrode 10, and is exposed to the outer surface of the discharge electrode 10 by the capillary phenomenon between the solution and the pores.

The vitamin C 50 derivative solution exposed to the outer portion of the discharge electrode 10 is externally evaporated by heat generation of the discharge electrode 10 or wind sent to the outer surface of the discharge electrode 10. Otherwise, power 30 is applied to the discharge electrode 10 and the ground electrode 20 to form an electric field. The vitamin C 50 derivative solution particles exposed to the outer surface of the discharge electrode 10 are transferred to the direction of the ground electrode 20 by the electrical force of the electric field.

Here, the vitamin C ($C_6H_8O_6$) is dissolved in $H_2O$ to discharge H$^+$, and thus transformed into dihydroascorbic acid that is an oxidization intermediate ($C_6H_7O_6^-$) having a negative polarity. The vitamin C 50 derivative is dissolved in $H_2O$ to be neutralized. Therefore, the vitamin C 50 derivative solution exposed to the surface of the discharge electrode 10 has a neutral polarity, and vapor of the vitamin C 50 derivative solution dispersed around the discharge electrode 10 also has a neutral polarity.

The electrons discharged from the discharge electrode 10 contact the vitamin C 50 derivative and the vapor having the neural polarity. Accordingly, the vitamin C 50 derivative is transformed into vitamin C ions ($C_6H_7NaO_6^-$) having a negative polarity. The vitamin C 50 ions ($C_6H_7NaO_6^-$) having the negative polarity are transferred to the direction of the ground electrode 20 by the electric field between the discharge electrode 10 and the ground electrode 20.

The electrons discharged from the discharge electrode 10 generate the vitamin C 50 ions ($C_6H_7NaO_6^-$) by contacting the vitamin C 50 derivative ($C_6H_7NaO_6$) evaporated on the outer surface and peripheral region of the discharge electrode 10, and move to the direction of the ground electrode 20. Some of the electrons discharged from the discharge electrode 10 generate $OH^-$ by contacting the vapor of the air between the discharge electrode 10 and the ground electrode 20.

Since most of the electrons are used to ionize the vitamin C 50 derivative, when some of the electrons move to the ground electrode 20, $OH^-$ is generated not to badly influence a human body. The thusly-prepared $OH^-$ is coupled with the bacteria of the air for oxidization.

FIGS. 7 and 8 illustrate an apparatus for measuring a discharge quantity of vitamin C 50 ions of the ion generator 70 in accordance with the present invention. The vitamin C 50 ions discharged from the discharge electrode 10 are housed in a measuring vessel 60 containing water, and a mass spectrum thereof is measured by a mass spectrometer. The vitamin C shows absorbance of 0.8 AU in a wavelength of 300 nm. The vitamin C is discharged from the discharge electrode 10.

Accordingly, generation of $OH^-$ is restricted by generation of the vitamin C 50 ions. The vitamin C 50 ions ($C_6H_7NaO_6^-$) are activated by the electrons from the discharge electrode 10, and give or receive $H^+$ to/from $OH^-$ generated by the electrons from the discharge electrode 10, thereby transforming some of $OH^-$ into $H_2O$ or $H_2$ in the air.

As illustrated in FIG. 6, the vitamin C 50 exists as a deoxidization type receiving two H atoms, and dehydroascorbic acid that is an oxidization type vitamin C 50 intermediate giving two H atoms. The vitamin C 50 performs a double chain reaction for giving or receiving two H atoms. The vitamin C 50 ions ($C_6H_7NaO_6^-$) discharged from the discharge electrode 10 move from the discharge electrode 10 to the ground electrode 20, and give or receive $H^+$ to/from $OH^-$, thereby neutralizing $OH^-$.

The vitamin C 50 ions are discharged from the discharge electrode 10 to the outer space of the air conditioner by the air sent by the ventilator of the air conditioner, for performing oxidization and deoxidization. The vitamin C 50 ions contact the skin of the human body or penetrate into the human body, to neutralize the free radicals generated in the human body.

The vitamin C 50 operated on the human body gives $H^+$ to $O_2^-$, $OH^-$, $H_2O_2^+$ and $LOOH^-$ that are free radicals existing in the human body, thereby transforming the free radicals into other substances such as $H_2O$ and preventing damages of cell walls of the free radicals and chromosomes. In addition, the vitamin C 50 gives $H^+$ to vitamin E for restricting fatty acid oxidization of the human body, thereby enabling the vitamin E wasted after anti-oxidization to perform anti-oxidization again. The vitamin C 50 itself is continuously activated by receiving $H^+$ from the enzyme inside human body such as glutathione.

As a result, in the operation of the air conditioner on which the ion generator 70 has been installed, the ion generator 70 discharging the vitamin C 50 ions can prevent excessive generation of $OH^-$ which is generated by electron discharge and has the detrimental effects on the human body, neutralize $OH^-$, and transmit the vitamin C 50 ions to the human body for anti-oxidization.

As discussed earlier, in accordance with the present invention, the ion generator improves its commercial value by generating and supplying the vitamin C essential for the human body.

In addition, the ion generator restricts generation of $OH^-$ by electron discharge, so that $OH^-$ cannot be operated as the free radical in the human body.

Furthermore, the ion generator discharging the vitamin ions can be applied to the air conditioner or the like, thereby improving a commercial value of the air conditioner.

Although the preferred embodiments of the present invention have been described, it is understood that the present invention should not be limited to these preferred embodiments but various changes and modifications can be made by one skilled in the art within the spirit and scope of the present invention as hereinafter claimed.

What is claimed is:

1. A vitamin ion generator, comprising:
   a discharge electrode for discharging electrons as well as evaporating vitamin derivatives by the application of power;
   a ground electrode having a different polarity from the discharge electrode, said ground electrode inducing the flow of electrons from the discharge electrode, and being grounded at a predetermined interval from the end of the discharge electrode;
   a reservoir connected to the discharge electrode said reservoir storing water and supplying said water to a housing groove formed in the discharge electrode; and
   vitamins disposed in the housing groove formed in the discharge electrode,
   wherein the discharged electrons ionize the evaporated vitamin derivatives into negatively ionized vitamin intermediates and vapor into $OH^-$.

2. The vitamin ion generator of claim 1, wherein the vitamins are vitamin C derivatives ($C_6H_7NaO_6$).

3. The vitamin ion generator of claim 1, wherein a plurality of pores are formed on the discharge electrode.

4. The vitamin ion generator of claim 1, wherein a casing is formed in a cylindrical shape outside the discharge electrode, for preventing the discharge electrode and the ground electrode from interfering with other members.

5. The vitamin ion generator of claim 1, wherein the discharge electrode and the ground electrode are installed inside a discharge outlet of an air conditioner, and the reservoir for collecting water generated in a heat exchanger of the air conditioner and the discharge electrode are connected through the hose.

6. The vitamin ion generator of claim 2, wherein the vitamin C derivatives contain sodium to improve the stability and coupling performance of vitamin C.

7. The vitamin ion generator or claim 1, wherein the housing groove which contains the vitamins circumscribes the discharge electrode which contains a plurality of pores and said reservoir is connected to the housing groove for conveying water to said vitamins, whereby the outer surface of the discharge electrode is exposed to vitamins dissolved in the water by capillary action through said plurality of pores formed on the discharge electrode.

\* \* \* \* \*